(12) United States Patent
Derchak et al.

(10) Patent No.: US 8,762,733 B2
(45) Date of Patent: Jun. 24, 2014

(54) SYSTEM AND METHOD FOR IDENTITY CONFIRMATION USING PHYSIOLOGIC BIOMETRICS TO DETERMINE A PHYSIOLOGIC FINGERPRINT

(75) Inventors: P. Alexander Derchak, Summit, NJ (US); Lance Myers, Ventura, CA (US)

(73) Assignee: adidas AG, Herzogenaurach (DE)

( * ) Notice: Subject to any disclaimer, the term of this patent is extended or adjusted under 35 U.S.C. 154(b) by 1436 days.

(21) Appl. No.: 11/627,198

(22) Filed: Jan. 25, 2007

(65) Prior Publication Data

US 2007/0177770 A1 Aug. 2, 2007

Related U.S. Application Data

(60) Provisional application No. 60/762,880, filed on Jan. 30, 2006.

(51) Int. Cl.
*G06F 21/00* (2013.01)

(52) U.S. Cl.
USPC ............................................ 713/186; 704/250

(58) Field of Classification Search
USPC .......................... 600/301, 534–535; 382/115
See application file for complete search history.

(56) References Cited

U.S. PATENT DOCUMENTS

| | | |
|---|---|---|
| 3,534,727 A | 10/1970 | Roman |
| 3,731,184 A | 5/1973 | Goldberg et al. |
| 3,874,368 A | 4/1975 | Asrican |
| 3,926,177 A | 12/1975 | Hardway, Jr. et al. |
| 4,016,868 A | 4/1977 | Allison ....................... 128/2.1 E |
| 4,033,332 A | 7/1977 | Hardway, Jr. et al. |
| 4,102,331 A | 7/1978 | Grayzel et al. |
| 4,258,718 A | 3/1981 | Goldman |
| 4,267,845 A | 5/1981 | Robertson, Jr. et al. |
| 4,289,142 A | 9/1981 | Kearns |
| 4,306,567 A | 12/1981 | Krasner ......................... 128/671 |
| 4,308,872 A | 1/1982 | Watson et al. ................. 128/725 |
| 4,373,534 A | 2/1983 | Watson ........................... 128/725 |
| 4,387,722 A | 6/1983 | Kearns |

(Continued)

FOREIGN PATENT DOCUMENTS

| | | |
|---|---|---|
| DE | 4214263 | 11/1993 |
| EP | 0262778 | 4/1988 |

(Continued)

OTHER PUBLICATIONS

Doddington, "Speaker Recognition—Identifying People by their Voices", 1985, IEEE, p. 1651-1664.*

(Continued)

*Primary Examiner* — Mahfuzur Rahman
*Assistant Examiner* — Gregory Lane
(74) *Attorney, Agent, or Firm* — Sterne, Kessler, Goldstein & Fox PLLC

(57) ABSTRACT

The invention provides a method for verifying a person's identity, which includes obtaining a password and/or random key from a person, and comparing the obtained password and/or random key to a plurality of known passwords and/or random keys to determine a likely identity of the person. The method further includes measuring a specific biometric of the person, the specific biometric comprising a respiratory, cardiac, or other physiologic biometric, and comparing the measured specific biometric to the known specific biometric of the person that is associated with the obtained password and/or random key to verify the likely identity of the person.

17 Claims, 8 Drawing Sheets

(56) References Cited

U.S. PATENT DOCUMENTS

| | | | |
|---|---|---|---|
| 4,433,693 A | 2/1984 | Hochstein | 128/721 |
| 4,446,872 A | 5/1984 | Marsoner et al. | |
| 4,452,252 A | 6/1984 | Sackner | 128/671 |
| 4,456,015 A | 6/1984 | Sackner | 128/721 |
| 4,463,764 A | 8/1984 | Anderson et al. | 128/719 |
| 4,494,553 A | 1/1985 | Sciarra et al. | |
| 4,537,196 A | 8/1985 | Phillipps et al. | |
| 4,546,777 A | 10/1985 | Groch et al. | |
| 4,548,204 A | 10/1985 | Groch et al. | |
| 4,549,552 A | 10/1985 | Groch et al. | |
| 4,572,197 A | 2/1986 | Moore et al. | |
| 4,580,572 A | 4/1986 | Granek et al. | |
| 4,648,407 A | 3/1987 | Sackner | 128/721 |
| 4,672,975 A | 6/1987 | Sirota | |
| 4,753,988 A | 6/1988 | Henton et al. | 525/73 |
| 4,777,962 A | 10/1988 | Watson et al. | |
| 4,796,639 A | 1/1989 | Snow et al. | 128/719 |
| 4,800,495 A | 1/1989 | Smith | 364/413.03 |
| 4,807,640 A | 2/1989 | Watson et al. | 128/721 |
| 4,815,473 A | 3/1989 | Watson et al. | 128/721 |
| 4,817,625 A | 4/1989 | Miles | 128/721 |
| 4,819,752 A | 4/1989 | Zelin | |
| 4,834,109 A | 5/1989 | Watson | 128/721 |
| 4,860,766 A | 8/1989 | Sackner | 128/748 |
| 4,863,265 A | 9/1989 | Flower et al. | |
| 4,867,571 A | 9/1989 | Frick et al. | |
| 4,911,167 A | 3/1990 | Corenman et al. | |
| 4,920,969 A * | 5/1990 | Suzuki et al. | 600/436 |
| 4,928,692 A | 5/1990 | Goodman et al. | |
| 4,934,372 A | 6/1990 | Corenman et al. | |
| 4,955,379 A | 9/1990 | Hall | |
| 4,960,118 A | 10/1990 | Pennock | 128/200.4 |
| 4,966,155 A | 10/1990 | Jackson | 128/671 |
| 4,972,842 A | 11/1990 | Korten et al. | 128/716 |
| 4,981,139 A | 1/1991 | Pfohl | |
| 4,986,277 A | 1/1991 | Sackner | 128/672 |
| 5,007,427 A | 4/1991 | Suzuki et al. | 128/659 |
| 5,025,791 A | 6/1991 | Niwa | |
| 5,036,857 A | 8/1991 | Semmlow et al. | |
| 5,040,540 A | 8/1991 | Sackner | 128/672 |
| 5,074,129 A | 12/1991 | Matthew | 66/192 |
| 5,076,801 A | 12/1991 | Schroll | |
| 5,099,841 A | 3/1992 | Heinonen et al. | |
| 5,099,855 A | 3/1992 | Yount | |
| 5,111,817 A | 5/1992 | Clark et al. | |
| 5,131,399 A | 7/1992 | Sciarra | 128/671 |
| 5,143,089 A | 9/1992 | Alt | |
| 5,159,935 A | 11/1992 | Sackner et al. | 128/721 |
| 5,173,151 A | 12/1992 | Namose | |
| 5,178,151 A | 1/1993 | Sackner | 128/672 |
| 5,224,479 A | 7/1993 | Sekine | |
| 5,241,300 A | 8/1993 | Buschmann | |
| 5,271,551 A | 12/1993 | Roepke | |
| 5,299,120 A | 3/1994 | Kaestle | |
| 5,301,678 A | 4/1994 | Watson et al. | 128/721 |
| 5,329,932 A | 7/1994 | Yount | |
| 5,331,968 A | 7/1994 | Williams et al. | 128/721 |
| 5,333,106 A | 7/1994 | Lanpher et al. | |
| 5,348,008 A | 9/1994 | Bornn et al. | 128/642 |
| 5,353,793 A | 10/1994 | Bornn et al. | 128/642 |
| 5,416,961 A | 5/1995 | Vinay | 128/165 |
| 5,447,164 A | 9/1995 | Shaya et al. | 128/710 |
| RE35,122 E | 12/1995 | Coreman et al. | 600/633 |
| 5,520,192 A | 5/1996 | Kitney et al. | |
| 5,533,511 A | 7/1996 | Kaspari et al. | 128/672 |
| 5,535,738 A | 7/1996 | Estes et al. | |
| 5,544,661 A | 8/1996 | Davis et al. | 128/700 |
| 5,564,429 A | 10/1996 | Bornn et al. | 128/696 |
| 5,577,510 A | 11/1996 | Chittum et al. | 128/709 |
| 5,582,337 A | 12/1996 | McPherson et al. | |
| 5,584,295 A | 12/1996 | Muller et al. | |
| 5,588,425 A | 12/1996 | Sackner et al. | 128/632 |
| 5,601,088 A | 2/1997 | Swanson et al. | 128/697 |
| 5,611,085 A | 3/1997 | Rasmussen | |
| 5,617,847 A | 4/1997 | Howe | |
| 5,694,939 A | 12/1997 | Cowings | 128/671 |
| 5,718,234 A | 2/1998 | Warden et al. | |
| 5,719,950 A | 2/1998 | Osten et al. | |
| 5,720,709 A | 2/1998 | Schnall | |
| 5,724,025 A | 3/1998 | Tavori | |
| 5,749,365 A | 5/1998 | Magill | 128/671 |
| 5,820,567 A | 10/1998 | Mackie | 600/519 |
| 5,825,293 A | 10/1998 | Ahmed et al. | |
| 5,848,027 A | 12/1998 | Dotter | 368/10 |
| 5,882,307 A | 3/1999 | Wright et al. | |
| 5,899,855 A | 5/1999 | Brown | 600/301 |
| 5,913,830 A | 6/1999 | Miles | 600/535 |
| 5,921,920 A | 7/1999 | Marshall et al. | |
| 5,937,854 A | 8/1999 | Stenzler | |
| 5,989,193 A | 11/1999 | Sullivan | |
| 5,991,922 A | 11/1999 | Banks | 2/69 |
| 6,002,952 A | 12/1999 | Diab et al. | |
| 6,015,388 A | 1/2000 | Sackner et al. | 600/529 |
| 6,018,677 A | 1/2000 | Vidrine et al. | |
| 6,035,154 A | 3/2000 | Takahata et al. | |
| 6,047,203 A | 4/2000 | Sackner et al. | 600/388 |
| 6,066,093 A | 5/2000 | Kelly et al. | 600/386 |
| 6,067,462 A | 5/2000 | Diab et al. | 600/310 |
| 6,068,568 A | 5/2000 | Kozakura et al. | 474/212 |
| 6,070,098 A | 5/2000 | Moore-Ede et al. | 600/544 |
| 6,120,441 A | 9/2000 | Griebel | |
| 6,142,953 A | 11/2000 | Burton et al. | 600/534 |
| 6,145,551 A | 11/2000 | Jayaraman et al. | |
| 6,198,394 B1 | 3/2001 | Jacobsen et al. | |
| 6,223,072 B1 | 4/2001 | Mika et al. | 600/510 |
| 6,254,552 B1 | 7/2001 | Lewis et al. | 600/603 |
| 6,261,238 B1 | 7/2001 | Gavriely | 600/532 |
| 6,273,859 B1 | 8/2001 | Remmers et al. | |
| 6,287,264 B1 | 9/2001 | Hoffman | |
| 6,302,844 B1 | 10/2001 | Walker et al. | 600/300 |
| 6,306,088 B1 | 10/2001 | Krausman et al. | |
| 6,341,504 B1 | 1/2002 | Istook | 66/172 E |
| 6,361,501 B1 | 3/2002 | Amano et al. | |
| 6,381,482 B1 | 4/2002 | Jayaraman et al. | |
| 6,413,225 B1 | 7/2002 | Sackner et al. | 600/529 |
| 6,436,057 B1 | 8/2002 | Goldsmith et al. | 600/586 |
| 6,443,890 B1 | 9/2002 | Schulze et al. | |
| 6,449,504 B1 | 9/2002 | Conley et al. | 600/523 |
| 6,454,719 B1 | 9/2002 | Greenhut | |
| 6,461,307 B1 | 10/2002 | Kristbjarnarson et al. | |
| 6,463,385 B1 | 10/2002 | Fry | |
| 6,478,736 B1 | 11/2002 | Mault | |
| 6,483,929 B1 | 11/2002 | Murakami et al. | |
| 6,485,431 B1 | 11/2002 | Campbell | |
| 6,506,153 B1 | 1/2003 | Littek et al. | |
| 6,511,424 B1 | 1/2003 | Moore-Ede et al. | 600/300 |
| 6,513,532 B2 | 2/2003 | Mault et al. | |
| 6,551,252 B2 | 4/2003 | Sackner et al. | 600/536 |
| 6,579,231 B1 | 6/2003 | Phipps | 600/300 |
| 6,604,115 B1 | 8/2003 | Gary, Jr. et al. | 707/104.1 |
| 6,633,772 B2 | 10/2003 | Ford et al. | 600/345 |
| 6,647,252 B2 | 11/2003 | Smith et al. | |
| 6,656,127 B1 | 12/2003 | Ben-Oren et al. | 600/532 |
| 6,687,523 B1 | 2/2004 | Jayaramen et al. | |
| 6,699,194 B1 | 3/2004 | Diab et al. | |
| 6,702,752 B2 | 3/2004 | Dekker | |
| 6,709,402 B2 | 3/2004 | Dekker | |
| 6,721,594 B2 | 4/2004 | Conley et al. | 600/523 |
| 6,723,055 B2 | 4/2004 | Hoffman | 600/538 |
| 6,726,636 B2 | 4/2004 | Der Ghazarian | 600/532 |
| 6,727,197 B1 | 4/2004 | Wilson et al. | 442/301 |
| 6,747,561 B1 | 6/2004 | Reeves | 340/573 |
| 6,775,389 B2 | 8/2004 | Harrison et al. | |
| 6,783,498 B2 | 8/2004 | Sackner et al. | 600/481 |
| 6,801,916 B2 | 10/2004 | Roberge et al. | 707/101 |
| 6,817,979 B2 | 11/2004 | Nihtila | |
| 6,858,006 B2 | 2/2005 | MacCarter et al. | |
| 6,881,192 B1 | 4/2005 | Park | 600/529 |
| 6,941,775 B2 | 9/2005 | Sharma | |
| 6,961,448 B2 | 11/2005 | Nichols et al. | 382/115 |
| 6,970,731 B1 | 11/2005 | Jayaramen et al. | |
| 6,993,378 B2 | 1/2006 | Wiederhold et al. | 600/509 |
| 7,001,337 B2 | 2/2006 | Dekker | |
| 7,073,129 B1 | 7/2006 | Robarts et al. | |

(56) References Cited

U.S. PATENT DOCUMENTS

| | | | |
|---|---|---|---|
| 7,077,810 | B2 | 7/2006 | Lange et al. |
| 7,081,095 | B2 | 7/2006 | Lynn et al. ................ 600/538 |
| 7,082,327 | B2 | 7/2006 | Houben |
| 7,099,714 | B2 | 8/2006 | Houben ................ 600/509 |
| 7,104,962 | B2 | 9/2006 | Lomask et al. ............ 600/529 |
| 7,154,398 | B2 | 12/2006 | Chen et al. |
| 7,207,948 | B2 | 4/2007 | Coyle |
| 7,254,516 | B2 | 8/2007 | Case, Jr. et al. |
| 7,267,652 | B2 | 9/2007 | Coyle et al. |
| 7,319,385 | B2 | 1/2008 | Ruha |
| 7,604,603 | B2 | 10/2009 | Sackner et al. |
| 7,670,295 | B2 | 3/2010 | Sackner et al. |
| 7,727,161 | B2 | 6/2010 | Coyle et al. |
| 7,762,953 | B2 | 7/2010 | Derchak et al. |
| 7,809,433 | B2 | 10/2010 | Keenan |
| 7,878,979 | B2 | 2/2011 | Derchak |
| 2002/0032386 | A1 | 3/2002 | Sackner et al. |
| 2002/0084130 | A1 | 7/2002 | Der Ghazarian ............ 600/532 |
| 2002/0090667 | A1 | 7/2002 | Ratcliffe et al. |
| 2002/0123701 | A1 | 9/2002 | Eriksen et al. |
| 2002/0138765 | A1 | 9/2002 | Fishman et al. |
| 2002/0138768 | A1 | 9/2002 | Murakami et al. |
| 2003/0100843 | A1 | 5/2003 | Hoffman |
| 2003/0135097 | A1 | 7/2003 | Wiederhold et al. |
| 2003/0135127 | A1 | 7/2003 | Sackner et al. ............ 600/536 |
| 2003/0185408 | A1 | 10/2003 | Causevic ................ 381/94.1 |
| 2003/0187341 | A1 | 10/2003 | Sackner et al. |
| 2004/0010420 | A1 | 1/2004 | Rooks |
| 2004/0019289 | A1 | 1/2004 | Ross |
| 2004/0030224 | A1 | 2/2004 | Sotos et al. |
| 2004/0041019 | A1 | 3/2004 | Schneider et al. |
| 2004/0111040 | A1 | 6/2004 | Ni et al. ................ 600/534 |
| 2004/0117204 | A1 | 6/2004 | Mazar et al. |
| 2004/0122334 | A1 | 6/2004 | Yamashiro |
| 2004/0143194 | A1 | 7/2004 | Kihara et al. ............ 600/534 |
| 2004/0204636 | A1 | 10/2004 | Diab et al. ............ 600/323 |
| 2004/0210147 | A1 | 10/2004 | Houben ................ 600/509 |
| 2004/0225227 | A1 | 11/2004 | Newman |
| 2004/0249299 | A1 | 12/2004 | Cobb ................ 600/529 |
| 2005/0027207 | A1 | 2/2005 | Westbrook et al. |
| 2005/0054941 | A1 | 3/2005 | Ting et al. ............ 600/529 |
| 2005/0076908 | A1 | 4/2005 | Lee et al. ............ 128/204.23 |
| 2005/0119586 | A1 | 6/2005 | Coyle et al. ............ 600/538 |
| 2005/0125970 | A1 | 6/2005 | Nolan |
| 2005/0211247 | A1 | 9/2005 | Noda et al. |
| 2005/0223236 | A1* | 10/2005 | Yamada et al. ............ 713/186 |
| 2005/0228234 | A1 | 10/2005 | Yang ................ 600/300 |
| 2005/0240087 | A1 | 10/2005 | Keenan et al. |
| 2005/0256385 | A1 | 11/2005 | Diab et al. |
| 2005/0264398 | A1* | 12/2005 | Siegel et al. ............ 340/5.52 |
| 2006/0000420 | A1 | 1/2006 | Davies et al. |
| 2006/0036183 | A1 | 2/2006 | Sackner et al. ............ 600/481 |
| 2006/0074334 | A1 | 4/2006 | Coyle |
| 2006/0122528 | A1 | 6/2006 | Gal |
| 2006/0178591 | A1 | 8/2006 | Hempfling ............ 600/529 |
| 2006/0258914 | A1 | 11/2006 | Derchak et al. |
| 2006/0293609 | A1 | 12/2006 | Stahmann et al. |
| 2007/0027368 | A1 | 2/2007 | Collins et al. |
| 2007/0049843 | A1 | 3/2007 | Derchak |
| 2007/0050715 | A1 | 3/2007 | Behar |
| 2007/0100622 | A1* | 5/2007 | Tavares ................ 704/250 |
| 2007/0150006 | A1 | 6/2007 | Libbus et al. |
| 2007/0177770 | A1 | 8/2007 | Derchak et al. |
| 2007/0208262 | A1 | 9/2007 | Kovacs |
| 2007/0209669 | A1 | 9/2007 | Derchak |
| 2007/0270671 | A1 | 11/2007 | Gal |
| 2008/0015454 | A1 | 1/2008 | Gal |
| 2008/0027341 | A1 | 1/2008 | Sackner et al. |
| 2008/0045815 | A1 | 2/2008 | Derchak et al. |
| 2008/0051839 | A1 | 2/2008 | Libbus et al. |
| 2008/0082018 | A1 | 4/2008 | Sackner et al. |
| 2008/0221401 | A1 | 9/2008 | Derchak et al. |
| 2008/0269644 | A1 | 10/2008 | Ray |
| 2009/0131759 | A1 | 5/2009 | Sims et al. |
| 2010/0274100 | A1 | 10/2010 | Behar et al. |
| 2011/0009766 | A1 | 1/2011 | McCool |

FOREIGN PATENT DOCUMENTS

| | | |
|---|---|---|
| EP | 0875199 A | 4/1998 |
| GB | 1596298 A | 8/1981 |
| GB | 2116725 | 9/1983 |
| JP | 53126786 A | 6/1978 |
| JP | 58109031 A | 6/1983 |
| JP | 6337933 A | 2/1988 |
| JP | 1091834 | 4/1989 |
| JP | 5168602 | 7/1993 |
| JP | 5298589 | 11/1993 |
| JP | 7227383 A | 8/1995 |
| JP | 2001516253 A | 9/1998 |
| JP | 2001104259 A | 4/2001 |
| JP | 2005-275508 | 10/2005 |
| WO | WO9810699 | 3/1998 |
| WO | WO 01/28420 | 4/2001 |
| WO | WO 01/76467 A2 | 10/2001 |
| WO | WO 02/060370 | 8/2002 |
| WO | WO0269878 | 12/2002 |
| WO | WO03022149 | 3/2003 |
| WO | WO2004/019503 | 10/2004 |
| WO | WO2005/115242 | 12/2005 |
| WO | WO 2006/002338 | 1/2006 |
| WO | WO 2006/009830 A2 | 1/2006 |
| WO | WO 2007/021645 | 2/2007 |
| WO | WO 2007/069111 A2 | 6/2007 |
| WO | WO2007/089751 | 8/2007 |
| WO | WO 2009/074973 A1 | 6/2009 |
| WO | WO 2010/027515 | 3/2010 |

OTHER PUBLICATIONS

Fahrenberg et al., "Origins and Developments of Ambulatory Monitoring and Assessment", Progress in Ambulatory Assessment. Seattle, WA: Hogrefe and Huber (2001).

SJSU Biometrics Publications, The Functions of Biometric Identification Devices, National Biometric Test Center.

SJSU Biometrics Publications, Biometric Technology Testing, Evaluation, Resuls, National Biometric Test Center.

6th Portuguese Conference on Biomedical Engineering,"BioEng' 2001 Conference Papers", (Jun. 2001) 6 pages.

Aliverti, A. et al., "Chronic Obstructive Pulmonary Disease: Regional Chest Wall Volumes During Exercise in Chronic Obstructive Pulmonary Disease." *Thorax*, 59:210-216, 7 pages, 2004.

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al., "Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

Blechert et al., "Identifying Anxiety States Using Broad Sampling and Advance Processing of Peripheral Physiological Information," *Psychosom Med* Dec. 2007;69(9):935-43 *Epub* Nov. 8, 2007 6 pages.

Bloch et al., "Specific respiratory patterns distinguish among human basic emotions," *International Journal of Psychophysiology*, 11:141-154 (1991), 14 pages.

Bonnet et al., "EEG Arousals: Scoring Rules and Examples, a Preliminary Report from the Sleep Disorders Atlas Task Force of the American Sleep Disorders Association," *Sleep*, 152(2): 173-184 (1992), 12 pages.

Brack, "Cheyne-Stokes respiration in patients with congestive heart failure," Swiss Med Weekly 133:605-610 (2003), 7 pages.

Costa et al., "Multiscale Entropy Analysis of Complex Physiologic Time Series," Physical Review Letters 89(6):068102-1-4 Aug. 5, 2002, 4 pages.

(56) References Cited

OTHER PUBLICATIONS

Coyle et al., "Home Measurement of Cough Indicates Circadian Frequency Pattern and Abnormal Distribution During Sleep," LifeShirt System, study sponsored by Pfizer, Inc., Jun. 2004, 1 page.
Gore Electronic Products, "Expanded PTFE Insulation Material", www.goreelectronics.com (visited Aug. 2005), 4 pages.
Grossman et al., "Reliability of Respiratory Tidal Volume Estimation by Means of Ambulatory Inductive Plethysmography," Biomed Sci Instrum 42:193-8 (2006), 6 pages.
Grossman et al., "A Comparison of Three Quantification Methods for Estimation of Respiratory Sinus Arrhythmia", Psychophycology, 27(6):702-714 (1990), 17 pages.
Istepanian et al., "Microcontroller-Based Underwater Acoustic ECG Telemetry System", IEEE Transactions on Information Technology in Biomedicine, 1(2):150-154 (Jun. 1997), 5 pages.
Keenan et al., "Adaptive Filtering of Heart Rate Signals for an Improved Measure of Sympathovagal Balance," Jan. 1, 2005, 8 pages.
Klabunde, "Electrocardiogram (EKG, ECG)", Cardiovascular Physiology Concepts, www.cvphysiology.com (visited Mar. 2005), 3 pages.
Lake et al., "Sample entropy analysis of neonatal heart rate variability," Am J Physiol Regul Integr Comp 283:R789-97 (2002), 10 pages.
Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001), 5 pages.
McCool et al., "Estimates of ventilation from body surface measurements in unstricted subjects," J. Appl. Physiol. 61(3):1114-9 (1986), 6 pages.
McCool et al., "Tidal Volume and Respiratory Timing Derived From a Portable Ventilation Monitor," Chest 122:684-91 (2002), 10 pages.
McNaughton et al., "Metallized Polymer Fibers as Leadwires and Intrafascicular Microelectrodes", J. Neurosci. Methods, 70(1):103-10 (1996), 2 pages.
Micro-Coax, "About Micro-Coax", www.micro-coax.com (visited Aug. 2004), 9 pages.
Niskanen et al., "Software for Advanced HRV Analysis", University of Kuopio Department of Applied Physics Report Series, pp. 1-11 (Feb. 2002), 12 pages.
O'Donnell, "Ventilatory Limitations in Chronic Obstructive Pulmonary Disease", Medicine & Science in Sports & Exercise, pp. S647-S655, (2001), 9 pages.
O'Donnell et al., "Dynamic Hyperinflation and Exercise Intolerance in Chronic Obstructive Pulmonary Disease", Am. J. Respir. Crit. Care Med., 164:770-777 (2001), 8 pages.
Park et al., "Automated Detection and Elimination of Periodic ECG Artifacts in EEG Using the Energy Interval Histogram Method", IEEE Transactions on Biomedical Engineering 49(12):1526-1533 (2002), 8 pages.
Pietraszek et al., "Simple Telemetry System for ECG Recording", Polish J. Med. Phys. & Eng. 2002; 8(3): 193-198, 4 pages.
Rampil, "A Primer for EEG Signal Processing in Anesthesia," Anesthesiology 89(4):980-1002 Oct. 1998, 15 pages.
Richman et al., "Physiological time-series analysis using approximate entropy and sample entropy," Am J. Physiol Circ Physiol 278:H2039-49 (2000), 11 pages.
Signal Consulting Inc., "Inductance of Circular Loop", www.sigcon.com (visited Aug. 2005), 2 pages.
Sijbers et al., "Reduction of ECG and gradient related arifacts in simultaneously recorded human EEG/MRI data," Magnetic Resonance Imaging 18:881-6 (2000), 6 pages.
Snyder et al., "Ventilatory Responses to Hypoxia and High Altitude During Sleep in Aconcagua Climbers," Wilderness and Environmental Medicine 18:138-145 (2007), 8 pages.
Szabo et al., "Prognostic Value of Heart Rate Variability in Chronic Congestive Heart Failure Secondary to Idiopathic or Ischemic Dilated Cardiomypathy," Am J Cardiol. 79:978-980 (1997), 3 pages.
van Dijk et al., "Determinants of Brachial Artery mean 24 h PulsePressure in Individuals with Type II diabetes mellitus and untreated mild hypertension", Clinical Science (2002), 102, pp. 177-186, 10 pages.
Vogiatzis, et al., "Respiratory Kinematics by Optoelectronic Plethysmography During Exercise in Men and Women.", Eur J of App Physiol, 581-587, 7 pages, 2004, 7 pages.
Wachowski, Andy and Larry, The Matrix, released Mar. 31, 1999 by Warner Bros. Pictures, see 1:26:29, 2:03:10, and 2:04:41, 13 pages.
Wilhelm et al., "Distinguishing Emotional From Physical Activation in Ambulatory Psychophysiological Monitoring," Biomed Sci Instrum 42:458-63 (2006), 6 pages.
Wilhelm et al., "Taking the laboratory to the skies: Ambulatory assessment of self-report, autonomic, and respiratory responses in flying phobia," Psychophysiology 35:596-606 (1998), 11 pages.
International Search Report and the Written Opinion of the International Searching Authority, application No. PCT/US06/60264, dated Jan. 15, 2008, 8 pages.
International Search Report and the Written Opinion of the International Searching Authority, application No. PCT/US2007/82688, dated May 8, 2008, 7 pages.
International Search Report and the Written Opinion of the International Searching Authority, application No. PCT/US2008/072414, dated Nov. 12, 2008, 7 pages.
International Search Report and the Written Opinion of the International Searching Authority, application No. PCT/US2008/061171, dated Nov. 14, 2008, 10 pages.
Supplementary Partial European Search Report of the European Patent Office, Application No. EP 06784447.2, dated Jan. 20, 2010, 9 pages.
Extended European Search Report for Application No. EP 07798146.2, Applicant: adidas AG, mailed Oct. 19, 2010.
Extended European Search Report for Application No. EP 10174873.9, Applicant: adidas AG, mailed Dec. 8, 2010.
Extended European Search Report for Application No. EP 10174680.8, Applicant: adidas AG, mailed Dec. 9, 2010.
Extended European Search Report for Application No. EP 10174876.2, Applicant: adidas AG, mailed Dec. 9, 2010.
Extended European Search Report for Application No. EP 10174881.2, Applicant: adidas AG, mailed Dec. 9, 2010.
Extended European Search Report for Application No. EP 10174683.2, Applicant: adidas AG, mailed Dec. 27, 2010.
Partial European Search Report for Application No. EP 10174885.3, Applicant: adidas AG, mailed Jan. 4, 2011.
Office Action dated Aug. 2, 2010 from U.S. Appl. No. 11/373,822, Sackner, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, filed Aug. 10, 2006.
Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.
Office Action dated Nov. 18, 2010 from U.S. Appl. No. 11/492,484, Behar, Computer Interfaces Including Physiologically Guided Avatars, filed Jul. 24, 2006.
Office Action dated Jan. 4, 2011 from U.S. Appl. No. 11/233,317,Gal, Improved Sensors for Inductive Plethysmographic Monitoring Applications and Apparel Using Same, filed Sep. 21, 2005.
Office Action dated Jan. 27, 2011 from U.S. Appl. No. 10/991,877, Keenan, Method and system for processing data from ambulatory physiological monitoring, filed Nov. 18, 2004.
Office Action dated Feb. 2, 2011 from U.S. Appl. No. 11/373,822, Sackner, System and Methods for Ambulatory Monitoring of Physiological Signs, filed Mar. 9, 2006.
U.S. Appl. No. 11/357,772, Sackner, System and Methods for Ambulatory Monitoring of Physiological Signs, filed Feb. 17, 2006.
U.S. Appl. No. 11/373,822, Sackner, System and Methods for Ambulatory Monitoring of Physiological Signs, filed Mar. 9, 2006.
U.S. Appl. No. 12/869,576, Stone, Method and System for Limiting Interference in Magnetometer Fields, filed Aug. 26, 2010.

(56) References Cited

OTHER PUBLICATIONS

U.S. Appl. No. 12/869,578, Derchak, Noninvasive Method and System for Monitoring Physiological Characteristics, filed Aug. 26, 2010.
U.S. Appl. No. 12/869,582, Derchak, Noninvasive Method and System for Monitoring Physiological Characteristics and Athletic Performance, filed Aug. 26, 2010.
U.S. Appl. No. 12/869,585, Derchak, Noninvasive Method and System for Monitoring Physiological and Athletic Performance Characteristics of a Subject, filed Aug. 26, 2010.
U.S. Appl. No. 12/869,586, Derchak, Physiological Database and System for Population Modeling and Method of Population Modeling, filed Aug. 26, 2010.
U.S. Appl. No. 12/869,592, Derchak, Multimodal Method and System for Transmitting Information About a Subject, filed Aug. 26, 2010.
U.S. Appl. No. 12/869,625, Derchak, Method and System for Interpretation and Analysis of Physiological, Performance, and Contextual Information, filed Aug. 26, 2010.
U.S. Appl. No. 12/869,627, Derchak, Physiological Monitoring Garment, filed Aug. 26, 2010.
U.S. Appl. No. 12/872,174, Derchak, Physiological Monitoring Garment, filed Aug. 31, 2010.
U.S. Appl. No. 12/971,193, Sackner, Systems and Methods for Ambulatory Monitoring of Physiological Signs, filed Dec. 17, 2010.
U.S. Appl. No. 12/976,080, Derchak, Methods and Systems for Monitoring Respiratory Data, filed Dec. 22, 2010.
Supplementary Partial European Search Report of the European Patent Office, Application No. EP 04759405.6, dated Jan. 24, 2011, 4 pages.
Office Action dated Feb. 1, 2011 from Japanese Appl. No. 2006-509897, Adidas AG, Systems and Methods for Respiratory Event Detection, Apr. 9, 2004.
Kohler, B., et al., "*The Principles of Software QRS Detection*," IEEE Engineering in Medicine and Biology (2002).
Scholkopf, B. et al., "*Estimating the Support of High-Dimensional Distribution, Neural Computation*," 13:7, 1443-1471, Massachusetts Institute of Technology (2001).
Supplementary European Search Report for Application No. EP 07 70 9881, The Hague, completed Jan. 28, 2010.

\* cited by examiner

SYSTEM AND METHOD FOR IDENTITY CONFIRMATION USING PHYSIOLOGIC BIOMETRICS TO DETERMINE A PHYSIOLOGIC FINGERPRINT

The application claims the benefit of U.S. Provisional Application No. 60/762,880 filed Jan. 30, 2006.

1. FIELD OF THE INVENTION

The present invention relates to a method for identifying a person. More particularly, the invention relates to a method of confirming the identity of a person using cardiac, pulmonary, or other biometric measurements.

2. BACKGROUND OF THE INVENTION

Systems designed for ensuring security and privacy can be used with a variety of applications. Such applications traditionally include the regulation of entry to, and mobility within, a person's residence or workplace, but can also include controlling access to a person's computer, vehicle, bank account, or other property.

Generally, these systems are premised on the idea of confirming the identity of a person as that of an authorized person or user before granting access to whatever the system is designed to protect. Typically, a security system solicits an identifier from a person, and the person in turn responds by providing such an identifier. A comparison is then made between the provided identifier and an identifier that is stored by the system and associated with the person's profile. If a correct match is made, access or entry is granted.

In the past, security systems have typically incorporated the solicitation of a password or other random key that is unique to an authorized person and which in theory only the authorized person knows or possesses. Some of the problems associated with passwords and keys, however, include the fact that they can be forgotten by, or otherwise become unavailable to, the authorized person. Furthermore, they can be discovered by, or otherwise be made known to or become possessed by, an unauthorized individual.

Security systems have also incorporated the solicitation of biometrics in their design, either alone or in conjunction with the solicitation of passwords or random keys. Some of the advantages of using biometrics include the fact that if properly selected, biometrics serve as relatively more precise and unique identifiers of a person and do not require active memory or possession of the identifier on the part of the person. Additionally, because properly selected biometrics are uniquely identifiable with only one specific person, the likelihood of falsifying or misrepresenting a person's biometric is relatively small. Biometrics that are currently used in security systems include superficial anatomical traits, for example fingerprints, hand and face geometries, and retinal patterns; cardiac parameters; metabolic parameters; vocal parameters; or other physiological characteristics.

The combination of a password and/or key, and a biometric adds to the reliability of identifying a unique individual. Even if all three parameters are incorporated, however, such a system may still be vulnerable to corruption. In a military setting, for example, an enemy combatant could steal the key from an authorized person, torture the person to acquire the password, and remove the person's finger to obtain the fingerprint biometric thereon, and thus potentially gain access to a military computer system.

Physiological data can be derived from a wide variety of physiological monitoring systems designed for, e.g., in-hospital use, in-clinic use, ambulatory use, or the like. Without limitation or prejudice, however, the following description is largely in terms of preferred monitoring systems for ambulatory use.

In order to perform normal daily waking and sleeping activities, a monitored subject should be constrained no more than necessary. In preferred embodiments, therefore, physiological sensors are attached to, affixed to, carried by, or incorporated in or as part of ordinary wearable items that are unobtrusive, comfortable, and useable without assistance. Suitable wearable items include garments, jackets, bands, patches, and the like, made from a variety of materials, particularly elastic materials to insure a snug fit; they can be donned in one piece or include zippers, Velcro, snaps, and the like, that are joined after donning. Sensors can be incorporated into garments in many ways, for example, by weaving, knitting, or braiding into a garment's fabric; or by being carried in, mounted in, or attached to the garment; also flexible sensors can be glued, printed, sprayed and so forth onto inner or outer garment surfaces. U.S. Pat. Nos. 6,551,252 and 6,047,203 disclose such garments. The entire contents of the references identified above are expressly incorporated herein by reference thereto. Citation or identification of the references listed above, or in any section of this application hereafter, shall not be construed as prior art to the present invention.

U.S. Pat. No. 5,719,950 describes a biometric authentication system that incorporates the solicitation of a specific biometric parameter, such as a fingerprint, and a non-specific biometric parameter, such as body temperature, electrocardiogram reading, or pulse. The non-specific biometric is selected to ensure that the individual seeking authentication is not incapacitated, dismembered, or deceased.

U.S. Pat. No. 6,483,929 describes a method and device for authentication using physiological and histological biometrics of a person, including fingerprints, muscular-skeletal dimensions, oxygen and carbon dioxide content in tissue, cardiac cycles, dilatory response of the eye, and other responses of the nervous and metabolic systems to applied stimuli.

Thus, there remains a need for a method of identity authentication and confirmation that measures as a biometric the unique set of multiple physiologic parameters and characteristics of a person, including for example respiratory and cardiac parameters.

3. SUMMARY OF THE INVENTION

The present invention is directed to a method for verifying a person's identity. A preferred embodiment includes obtaining a password and/or random key from a person and comparing it to a plurality of known passwords and/or random keys to determine a likely identity of the person. The method also includes measuring a specific biometric of the person, and comparing it to the known baseline specific biometric of the person that is associated with the obtained password and/or random key to verify the likely identity of the person. Preferably, the known baseline respiratory biometric includes a range of values.

Preferably, the measured specific biometric includes a respiratory biometric. Additionally, the respiratory biometric of the person preferably includes a respiratory rate, a minute ventilation, a tidal volume, an inspiratory flow rate, an expiratory flow rate, a presence of cough, and presence of apnea or hypoapnea, or a combination thereof. Measuring the respiratory biometric preferably includes measuring the thoracic and/or abdominal girth of the person. Preferably, a person's girth is measured by inductive plethysmography.

In one embodiment, measuring the respiratory biometric preferably includes instructing the person to perform one or more maneuvers, and measuring at least one respiratory pattern exhibited by the person during performance of the maneuvers. The measured respiratory biometric includes at least one measured respiratory pattern. The at least one respiratory pattern is preferably measured over a period time during the performance of the maneuvers. Preferably, at least one maneuver includes performing a predetermined sequence of breaths, and at least one maneuver includes performing a predetermined sequence of physical movements.

In another embodiment, the specific biometric preferably further includes other physiological parameters, such as cardiac parameters, posture/activity parameters, temperature parameters, EEG parameters, EOG parameters, EMG parameters, vocal parameters, and gait parameters, or a combination thereof. In particular, the cardiac parameters preferably include an ECG parameter.

In yet another embodiment, the method further includes obtaining at least one of a fingerprint, a retinal scan, an electrocardiogram, and a DNA scan from the person, comparing the at least one obtained fingerprint, retinal scan, electrocardiogram, and DNA scan to a plurality of known fingerprints, retinal scans, electrocardiograms, and DNA scans to determine a likely identity of the person, and comparing the measured specific biometric to the known baseline specific biometric of the person that is associated with the fingerprint, retinal scan, electrocardiogram, and DNA scan to verify the likely identity of the person.

The present invention is also directed to a method for verifying a person's identity by providing an ambulatory measuring device to a person configured for measuring a specific biometric of the person, measuring the specific biometric of the person, and comparing the measured specific biometric to a database of known baseline specific biometrics to verify the identity of the person. In one embodiment, the specific biometric includes a respiratory biometric, while in another embodiment, the specific biometric includes an ECG parameter. Preferably, the ambulatory measuring device includes a garment that is worn by the person.

The invention thus provides an method of confirming the identity of a person that includes measuring a unique parameter or set of multiple physiologic parameters of the person. This invention also includes software products implementing the methods of this invention. Hardware systems variously configured to perform the methods of this invention are also included.

4. BRIEF DESCRIPTION OF THE DRAWINGS

The present invention may be understood more fully by reference to the following detailed description of preferred embodiments of the present invention, illustrative examples of specific embodiments of the invention, and the appended figures in which.

5. DETAILED DESCRIPTION OF THE PREFERRED EMBODIMENTS

Figure 1:
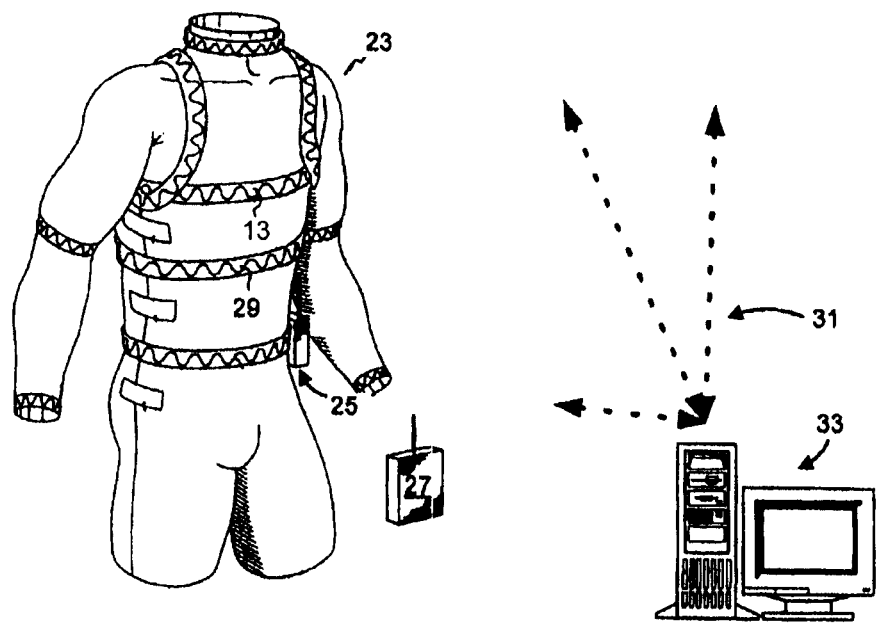
FIG. 1 depicts an embodiment of an ambulatory multiple parameter monitoring system according to the present invention.

Preferred embodiments of the present invention include monitoring of specific biometrics of a person including, for example, moment-by-moment cardiac and pulmonary functioning, activity level, and other physiological systems or processes. Particular embodiments may monitor fewer physiological systems, while other embodiments may monitor additional physiological systems depending on the availability of ambulatory, non-invasive sensors.

Many types of sensors can be incorporated in wearable, monitoring items. One useful physiological sensor, referred to herein generically as a "size sensor", gathers signals responsive to size indicia describing portions of a monitored subject's body, e.g., the torso, the neck, the extremities, or parts thereof. Size indicia can include the length along a selected portion of the body surface; the circumference, diameter, or cross-sectional area of a body part; and the like.

Size sensor signals can also be processed to yield information about organ system functioning. Signals from size sensors at one or more levels of the torso, e.g., at an abdominal level and at a rib cage level, can be interpreted using a two-component breathing model in order to determine respiratory rates, respiratory volumes, respiratory events, and the like. U.S. Pat. Nos. 6,551,252; 5,159,935; and 4,777,962, and U.S. patent application Ser. No. 10/822,260 describe such signal processing. Indicia from size sensors at the mid-thorax can be processed to determine cardiac stroke volumes and/or aortic pulsations. U.S. Pat. Nos. 6,783,498 and 5,178,151 describe such signal processing. Additionally, size sensors about one or more limbs can be responsive to venous or arterial pulsations, the changing size of an extremity, and the like; and abdominal size sensors can also be responsive to intestinal activity, and so forth. U.S. Pat. No. 5,040,540 describes such sensors.

Preferred size sensors are based on inductive plethysmographic ("IP") technologies. However, useful size sensors can be based on diverse other technologies, e.g., body impedance sensors; mercury-containing silastic strain gauges; differential linear transformers; magnetometers sensing body diameters; piezoelectric or mechanical strain gauges; magnetic motion detectors; various optical techniques including interferometry; electrical impedance; surface electrical or magnetic activity; ultrasonic and Doppler measurements of body wall motions or body diameters; and/or plethysmographic techniques including bellows pneumographs, volume pneumographs, body plethysmographs, and so forth. Active elements of size sensors can be based on thread and fabric technologies. A fabric size sensor can measure, e.g., the resistance of conductive threads; the optical properties of transparent threads; the local strain of a fabric woven so that local strain is reflective of circumferential overall strain, and so forth.

With respect to preferred sensors based on IP technologies, the impedance of a conductive element is known to reflect size and shape of the element. Therefore, the impedance of a conductive element configured to lie on a portion of a body part, to partially or fully encircle a body part, or otherwise arranged on the body of a subject changes as the size of the underlying body part changes due to, e.g., respirations, pulsations, voluntary motions, cardiac activity, and the like. IP technology measures this impedance and consequently reflects such physiological functioning.

An IP sensor includes a conductive element, usually a loop of wire or a conductive thread, arranged so that its impedance changes, preferably substantially linearly, with its size and shape. So that IP sensors generate signals reflective of changes in the size of the underlying body part, these sensors are conveniently incorporated in elastic material arranged alone or in a garment to fit snugly against the monitored body part. The elastic material can be a knitted, woven, crocheted, or braided textile on which the sensor wire or thread is affixed during or after textile manufacture. Sensor electronics then determines the impedance, preferably substantially inductive, of an IP sensor's conductive element. In preferred embodiments, the IP sensor is incorporated into a resonant circuit and changes in resonant frequency are measured, e.g., by using a counting oscillator. Digitized data reflecting the time varying resonant frequencies are then output for processing into physiological information.

In addition to size sensors providing respiratory and/or cardiac information, wearable items can include diverse additional sensors for other physiological and/or non-physiological parameters of a monitored subject. For example, accelerometers can sense current activity level and body posture or orientations including signals relating to a person's walking gait or pace; thermistors can sense skin or body core temperature; and pulse oximeters can sense blood oxygen level. Further, electrodes in electrical communication with the subject can sense such electrical activities as electrocardiogram ("ECG") signals, electroencephalogram ("EEG") signals, electro-oculogram ("EOG") signals, electro-myogram ("EMG") signals (of the orbital, facial and other muscles), skin conductance or resistance, and the like. These electrodes are preferably made of fabric, or are otherwise flexible, and provide sufficient electrical contact without the need for conductivity enhancements, such as pastes, fluids, and the like. Additional sensors can include microphones for vocal and body sounds, ultrasound transducers for blood flow or organ pulsations, and so forth.

5.1 PREFERRED MONITORING SYSTEMS

Preferred embodiments of physiological monitoring systems include sensors that gather signals for processing. In one embodiment, the monitoring system includes sensors, as generally known to one of ordinary skill in the art, that can be constructed according to the many known technologies useful for non-invasive physiological sensing. Preferably, selected sensors have sufficient accuracy and precision, both in amplitude and response time (i.e. bandwidth), so that the gathered signals actually reflect the physiological systems and processes of interest. Preferably, the sensors have clinically confirmed accuracies and precisions.

Preferably, the physiological monitoring systems are ambulatory systems configured so that a person is not constrained and can perform their normal daily waking and sleeping activities. Preferably, the ambulatory monitoring systems are also configured for use without assistance by medical or other trained personnel. A preferred ambulatory physiological monitoring system configuration includes a wearable item, for example, a garment, band, patch, and the like, or associations with partial-shirts or shirts, on partial body suits, or in full body suits that are unobtrusive, comfortable, and preferably made of non-restricting fabric into which sensors are incorporated.

A preferred embodiment of an ambulatory monitoring systems is illustrated in FIG. 1, which depicts garment 23 equipped with an extensive array of size sensors capable of measuring venous and arterial pulsations, individual lung function, and the like, as well as other sensors. In particular, size sensor 13 located around the thorax of an individual measures anatomical changes thereat and returns signals relating to respiratory function. Additionally, size sensor 29 at the mid-thorax level of the xiphoid process returns signals with cardiac pulsation components. This embodiment is provided with two buffering and/or processing units (referred to herein as portable date units ("PDUs"), local unit 25 and nearby unit 27. PDUs are preferably sufficiently compact and lightweight to be carried on or by the monitored subject. PDUs can include IP sensor electronics and preferably also electronics for operating sensors, and (if necessary) retrieving and digitizing sensor data. Such systems are described in U.S. Pat. No. 6,551,252.

Signals gathered by monitoring systems for use by this invention are preferably processed by one or more analysis computers providing processing capability that may be remotely located or distributed. Preferably, the processing methods are linked into an integrated system that processes signals from a monitoring system primarily directed to cardio-respiratory monitoring. In one embodiment, basic signal processing, e.g. filtering and digitization, is performed on units local to the monitoring system, such as local unit 25. Complete processing by this invention's methods generally requires processing capabilities similar to those of a modern desktop PC with, for example, a 2 GHz or more processor, 256 MB or more of main memory, 10 GB or more of peripheral storage, standard interface units, and the like. In one embodiment, nearby unit 27 provides this capability in the vicinity of the monitored person, while in another embodiment, this capability is provided by remotely located system 33. Gathered signal data is transferred to system 33 and unit 27 by routine means, for example, using private wireless networks or public cellular phone systems, by means of a memory device such as a micro hard disk or a flash memory card, and the like.

Initial sensor signal processing generally includes filtering, digitization, noise limiting, extraction of relevant signal components, and the like. Following initial processing, specific processing of respiratory size sensor signals includes calibration, determination of a tidal volume signal, and extraction of respiratory events from the tidal volume signal. U.S. Pat. Nos. 6,413,225; 5,159,935; 4,834,766; and 4,777,962, and U.S. patent application Ser. No. 10/822,260 describe such respiratory processing. Cardiac sensor signal processing includes extraction of cardiac components, enhancement of cardiac components, determination of stroke volume indicia, and the like. U.S. Pat. Nos. 6,783,498; 5,178,151; and 5,040,540, and U.S. patent application Ser. No. 10/991,877 describe such cardiac processing.

Signals from additional sensors are processed as appropriate. R-wave can be recognized in ECG signals using known methods, and then cardiac rates and rate variability can be extracted. ECG, EMG, EOG, and similar signals are usually stored for later manual grading and analysis. Accelerometer signals can be low and high pass filters to extract posture information and activity level information, respectively. U.S. patent application Ser. No. 10/991,877 describes such signal processing.

This methods of the present invention are performed on software or firmware programmable systems. In the case of software programming, methods are coded in standard computer languages, such as C, C++, or in high level application languages, such as Matlab and associated toolboxes (Math Works, Natick, Mass.). Code is then translated or compiled into executable computer instructions for controlling a microprocessor or similar device. In the case of firmware programming, higher level method specifications written in software languages or hardware languages such as VHDL, are generally translated into bit codes by tools supplied by the manufacturer of the hardware part that is being programmed. For example, manufacturer's tools prepare bit-streams for configuring FPGAs.

Software or firmware programming can be stored and transferred on computer readable media (such as CD ROMS, flash cards, etc.), across-network connections, and the like. This programming can be made generally available as program products.

5.2 PREFERRED IDENTIFICATION METHODS

The present invention preferably includes methods and systems of verifying a person's identity that compare physiological information recorded at a time of identity confirmation with baseline physiological information recorded previously, the physiological information being preferably measured by embodiments of the physiological monitoring systems and methods previously described. Preferably, the present invention can be incorporated into existing or new systems, such as security systems, access control systems, and the like, that authorize only those persons who meet various identification criteria.

Figure 2:
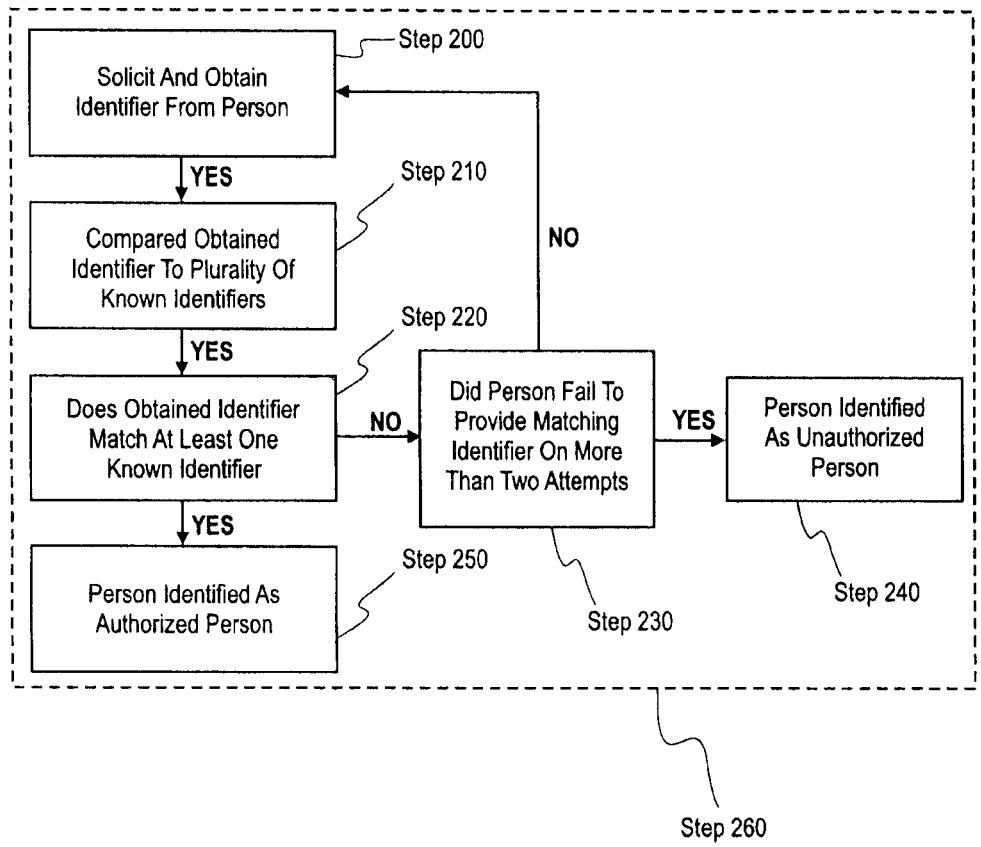
FIG. 2 depicts one embodiment of a method of identifying a person as known in the prior art.

FIG. 2 depicts one example of a prior art method 260 of identifying a person that includes soliciting and obtaining from a person an identifier, which may include a password and/or a random key, as shown in step 200. In some cases, the password is a personal identification number ("PIN") or an alphanumeric combination, for example a text string, that is either manually entered on a keypad or spoken aloud by the person for processing and recognition by the system. In some cases, the random key includes a physical key configured for receipt in a keyhole, or an electronic access card, badge, or fob that is configured to be read by an electronic sensor or reader. In other embodiments, the identifiers may include digital images, fingerprints, retinal scans, DNA scans, and/or electrocardiogram readings, and the like, which are obtained by known methods for processing by the system.

Once the identifier is obtained from the person, it is compared to a plurality of known baseline identifiers, as shown in step 210, and the system determines if there is a match, as shown in step 220. Typically, these identifiers are previously recorded, and stored in an electronic database of the system. The stored identifiers correspond to a list or profiles of "authorized persons", i.e., those persons who are authorized, for example, for entry or access.

If the identifier obtained from the person does not match or correspond to at least one of those stored in the database, solicitation of the person's identifier is repeated as shown in step 230. If the person continually (for example, more than twice) provides an identifier that does not match or correspond to at least one that is stored in the database, the person is identified as an "unauthorized person," as shown in step 240. As a result, and if, for example, the method was incorporated in a security system, the person would be denied access or entry to the property that the system is protecting. If, however, the person provides an identifier that matches or corresponds to at least one identifier stored in the database, the person is recognized as an "authorized person," and is granted access or entry, as shown in step 250.

Such prior art methods of identification, however, typically suffer from many disadvantages, as previously discussed. The present invention supplements known identification systems with additional steps to verify and confirm the identity of a person based on indices derived from physiological measurements after initial recognition that a person is a "likely authorized person".

Figure 3:
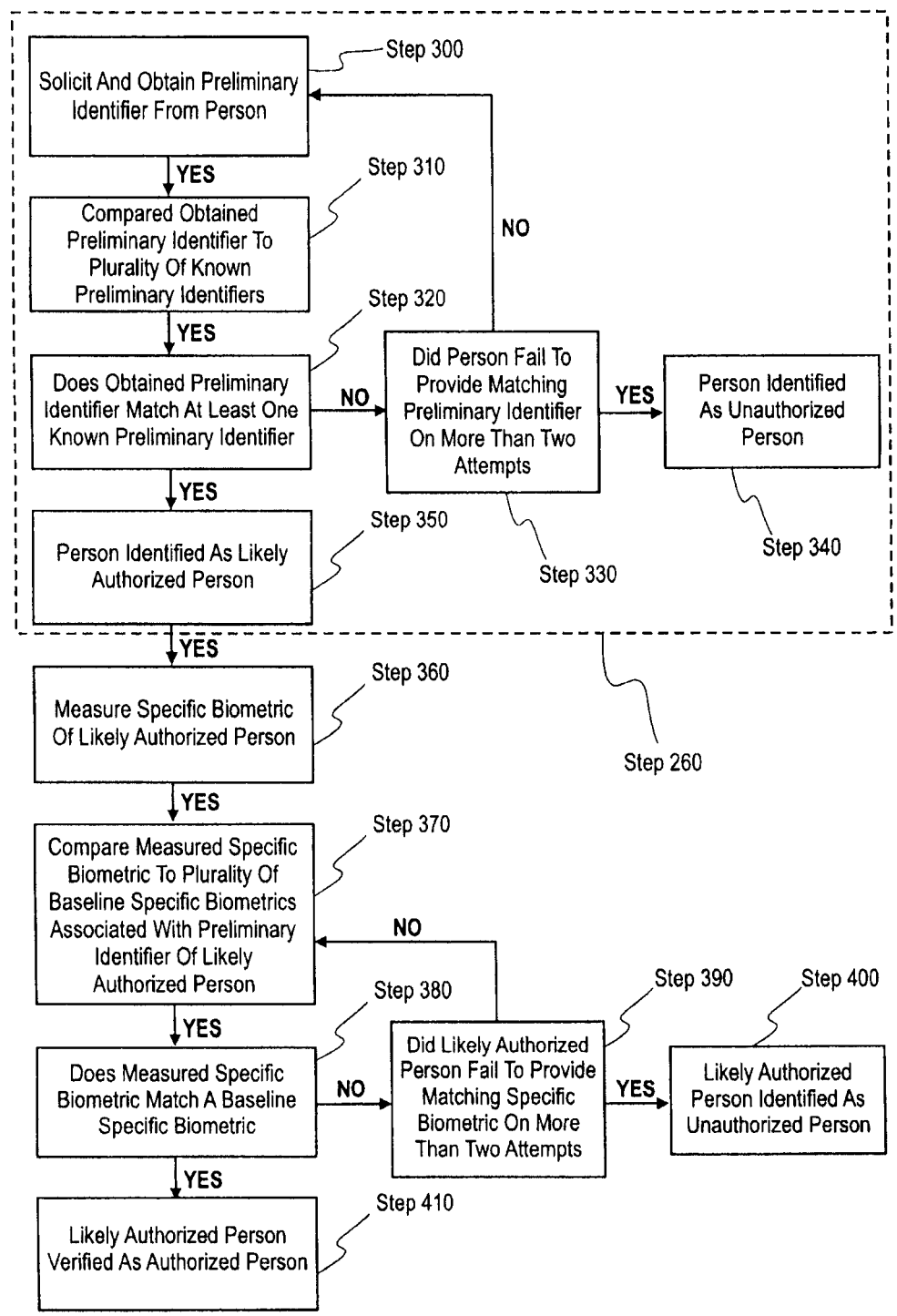
FIG. 3 depicts one embodiment of a method of confirming the identity of a person according to the present invention.

A preferred embodiment of the method of the present invention is depicted in FIG. 3. Preferably, steps 300 to 350 are similar to steps 200 to 250 of the prior art method 260 shown in FIG. 2. Specifically, the steps of soliciting and comparing a "preliminary identifier" in FIG. 3 are analogous to those for soliciting and comparing an "identifier" in FIG. 2, and the step of identifying a person as a "likely authorized person" in FIG. 3 is analogous to that for identifying a person as an "authorized person" in FIG. 2.

After identifying a person as a likely authorized person in step 350, the preferred method further includes measuring a specific biometric of the likely authorized person that includes at least one physiologic biometric, for example a respiratory biometric, as shown in step 360. As previously described, the respiratory biometric preferably includes discrete indices such as a respiratory rate, a minute ventilation, a tidal volume, an inspiratory or expiratory flow rate, a presence of a cough, apnea, or hypoapnea, or a combination thereof. Preferably, the respiratory biometric is measured by measuring the size or girth of the likely authorized person's thorax and/or abdomen. As previously discussed, measurement is preferably achieved by using IP sensors incorporated in a garment or other similar ambulatory device to measure changes in cross-sectional areas, circumferences, diameters, or geometrically similar indicia of the person's thorax and/or abdomen.

Aside from measuring discrete or single physiological parameters as a specific biometric of a person, the method can also include measuring a person's physiological response to stimuli or other provocations. In one embodiment, the likely authorized person's respiratory biometric is measured as a series of responses or waveforms over a selected period of time to provide a "physiological fingerprint" of the likely authorized person.

Preferably, such a physiological fingerprint is measured by instructing the person to perform a physical maneuver and measuring at least one physiological parameter, for example a respiratory pattern, exhibited by the person while performing the maneuver. The person can be instructed to perform a series of physical maneuvers over a period of time, for example five, ten, or thirty seconds, while measurements of respiratory patterns are obtained. Additionally, measurements can be taken over a period of time after the person performs the maneuvers to capture the person's exhibited response to, or recovery from, the maneuvers.

In one example, the person may be instructed to perform a series predetermined inhalation and exhalation breathing patterns, such as deep breaths and short breaths, and the person's measured inspiratory and expiratory flow rates and/or capacities are measured. Alternatively, the person may be instructed to perform a series of predetermined physical movements or exercises, such as jumping-jacks or stationary jogging, and the person's respiratory response while performing the exercises is measured as a biometric. The physiological fingerprint can also include measurements of other physiological parameters as the specific biometric of the likely authorized person.

Once the likely authorized person's specific biometric is measured, the measured specific biometric is compared to a plurality of known baseline specific biometrics that are associated with the preliminary identifier of the likely authorized person, as shown in step 370, and the system determines if there is a match, as shown in step 380. These baseline specific biometrics are also stored in the electronic database of the system. Preferably, the baseline specific biometric is previously measured at a time when the person exhibited a stable physiological condition and health to reflect the person's normal physiological parameters. Additionally, the baseline specific biometric is preferably recently updated, e.g., preferably measured within the last five years and more preferably measured within the twelve months, to minimize expected deviations due to aging.

Preferably, the baseline specific biometric of a person is stored as a limited range of discrete indices or physiological fingerprints. For example, the method can include measuring a person's baseline respiratory rate, and storing such respiratory rate as a baseline specific biometric that includes a range of respiratory rates, i.e., having upper and lower bounds that differ by a percentage of the measured respiratory rate. Preferably, the allowable range is determined based on a normal deviation that can be expected in a healthy population for a particular physiological parameter; more preferably, the allowable range is less than a normal deviation. By storing the baseline specific biometric as a limited range, the comparison during step 370 does not have to result in an exact match in step 380. Rather, so long as the measured specific biometric of a person falls within an acceptable tolerance range of the baseline specific biometric, a correct match will be determined.

In the case of physiological fingerprints comprising a series of physiological measurements, such as a time series of respiratory measurements, the methods can preferably also include comparing such fingerprints and determining the likelihood of a match by known pattern recognition techniques. See, e.g., Duda et al., *Pattern Classification,* 2000 2'nd ed., Wiley-Interscience. Such techniques can be, for example, based on statistical classifications, or on neural networks, or the like. A preferred type of pattern recognition technique is described subsequently with respect to ECG recognition. In the case of a time series of respiratory measurements, significant features can readily be determined and the described techniques can be readily adapted.

If the measured specific biometric of the likely authorized person does not match or correspond one of those baseline specific biometrics that are stored in the database and associated with the preliminary identifier of that person, measuring of the likely authorized person's specific biometric is repeated, as shown in step 390. If, after successive attempts (for example, more than twice), the measured specific biometric does not match or correspond to one of the baseline specific biometrics stored in the database for the likely authorized person, the likely authorized person is verified and confirmed as an unauthorized person, as shown in step 400.

If, however, the measured specific biometric of the likely authorized person matches or corresponds to one of the baseline specific biometrics stored in the database and associated with the preliminary identifier for that person, the identity of the likely authorized person is verified and confirmed as that of an authorized person, as shown in step 410. As a result, and if, for example, the method were incorporated in a security system, the person would be granted access or entry.

In alternative embodiments, the measured specific biometric preferably includes, in addition to a respiratory biometric, or alternatively, standing alone, other physiological parameters, such as cardiac parameters (including heart rate, ECG readings, and blood pressure), posture and activity parameters, temperature parameters, EEG, EOG, and EMG parameters, speech and cough parameters (including pitch, frequency, and amplitude), gait or other walking parameters, or a combination thereof. These specific biometrics can be measured by known techniques as were previously discussed, and preferably include the use of IP sensors incorporated in a garment or other ambulatory device.

5.3 PREFERRED PARAMETER RECOGNITION METHODS

The identification methods previously discussed are preferably based on or incorporate standard pattern recognition and machine learning tools as known in the art. See, e.g., Duda, R. et al., *Pattern Classification*, Wiley, New York, N.Y. (2001), Vapnik, V., *Statistical Learning Theory*, Wiley, New York, N.Y. (1998), and Hastie, T. et al., *The Elements of Statistical Learning*, Springer (2001).

Figure 4:
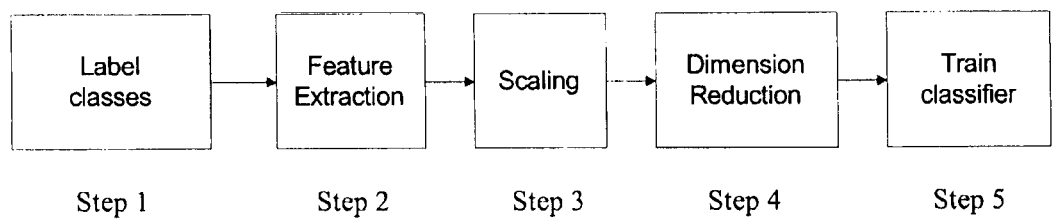
FIG. 4 depicts a flow chart for one embodiment of a training algorithm.

Pattern recognition may be broadly defined as developing an automated algorithm that is able to accurately classify an individual as belonging to one of n labeled classes. The basic approach preferably includes a-priori data to train an algorithm. Presentation of this data to a classification algorithm teaches the classifier to generalize between each of the classes that are present. Thus, the classifier preferably creates a set of decision boundaries so that when a new data point is presented to the classifier, the classifier may label it accordingly. FIG. 4 is a flow chart that shows steps 1-5 of one embodiment for training a classification system for use in pattern recognition.

Step 1 preferably includes labeling the relevant classes. Preferably, this is simply assigning an arbitrary integer label for each of the n classes or individuals, e.g., $c_1=1, \ldots, n$. Step 2 preferably includes extracting relevant features from the data that will be used to uniquely identify each class. In many embodiments, sets of features are manually selected and the remaining steps of FIG. 4 are performed to determine if the performance of the trained classifier is satisfactory. If not, a different set of features is manually selected and the process of FIG. 4 is repeated. Other embodiments of this invention include automatically selecting features; performing the steps of FIG. 4 to determine whether the classifier performance is satisfactory; and if not, returning to step 2 and repeating this process with another automatically determined set of features. The extracted features are put together to form a feature vector. The dimension D of this vector or feature space is preferably the number of features used, and each component in the feature vector is preferably a scalar component. Following feature extraction, step 3 preferably includes scaling the data in an appropriate manner. In one embodiment, this is a simple transform that ensures that the data lie in the range [0;1] or [−1;1].

The dimension reduction of step 4 preferably includes principal components analysis to transform a number of correlated variables into a preferably smaller number of uncorrelated variables called principal components. This allows the first principal component to account for as much of the variability in the data as possible, and each succeeding component then accounts for as much of the remaining variability as possible. As a result, components that account for very little variability in the feature space may be discarded.

The final step 5 includes selection of an appropriate learning algorithm to train the classifier. Preferably, the scaled and reduced feature vectors used for training are presented to the learning algorithm, i.e., for each class, a representative set of training data is labeled as belonging to that class. The algorithm then preferably fits hyper-dimensional decision boundaries between each class. A preferred learning algorithm for identity confirmation is the one-class support vector machine ("SVM"), see e.g. B. Scholkopf et al., Estimating the Support of High-Dimensional Distribution, Neural Computation, 13:7, 1443-1471 (2001). Embodiments of this invention also include automatically selecting important features by repeating the steps of FIG. 4 until the performance of the trained classifier is satisfactory.

Figure 5:
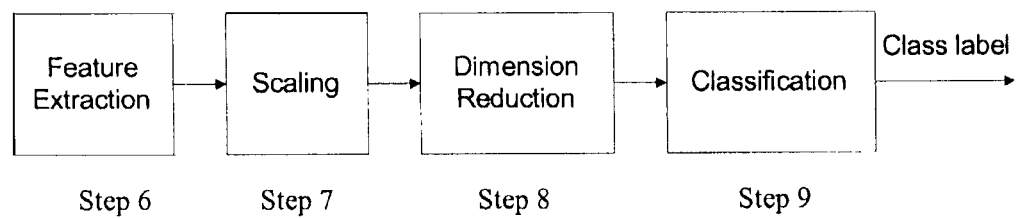
FIG. 5 depicts a flow chart for one embodiment of a classifying algorithm.

Once a system has been trained, new data may be classified, as shown in FIG. 5. Steps 6-8 are generally similar to steps 2-4 except that the former steps make use of information determined by the latter steps. Specifically, steps 6-8 use the features and also use the characterizations of reduced dimensionality that have been determined during training during steps 2 and 4, respectively, to be significant and useful. Where step 4 applies a principal components analysis, the characterizations of reduced dimensionality are the important principal components, each of which is a combination of one or more of the extracted features. Further, step 9 uses the classifier that has been trained in step 5.

Thus, classification step 6 receives input signals describing an subject and extracts the particular features of importance determined during training. Step 7 scales the extracted features in a manner similar to the scaling performed in step 3. Step 8 combines the scaled features into the important characterizations of reduced dimensionality that have been previously determined during training. Then step 9 applies the previously-trained classifier to the characterizations determined in step 8 in order to find the likely class (if any) for the subject described by the input signals.

In the present invention, the class of an subject being tested is determined to be one the classes of the subjects on which the method has been trained. Each such training class is further identified by its identifies (see, e.g., FIG. 2). If the determined class matches the class identified by the identifier presented by the subject under test, then that subject is indicated to be confirmed. If the determined and the identified classes do not match, or if no likely matching class is found, the subject is indicated to be not confirmed.

ECG Parameter Recognition

A preferred parameter recognition method for measuring ECG as a specific biometric is described below in more detail. Extracted features can be combined to form a feature vector that is preferably used as the primary representation or indicator for comparing measured physiological parameters to baseline physiological parameters.

Figure 6:
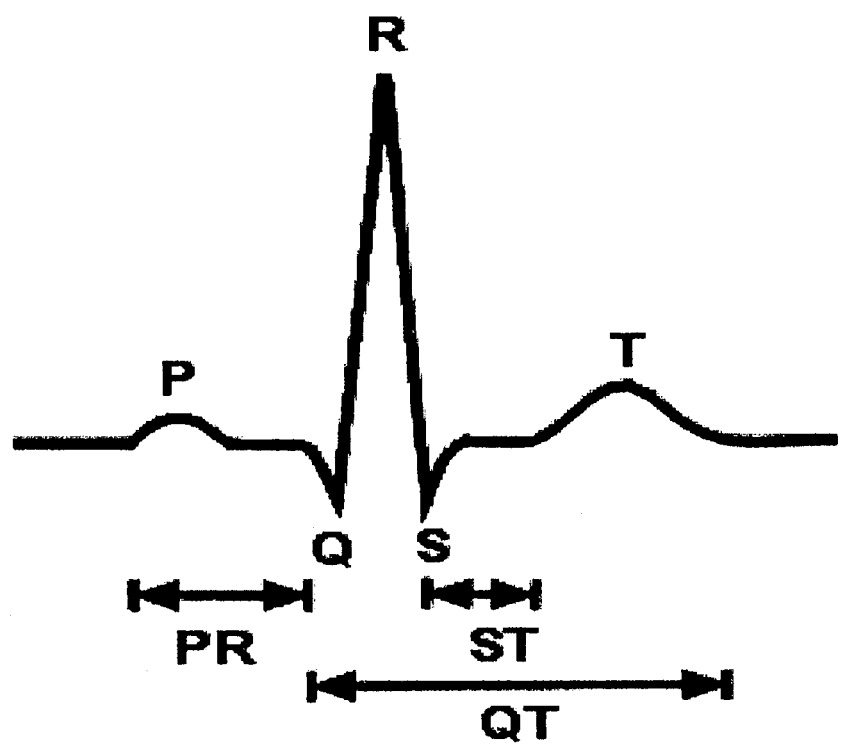
FIG. 6 depicts an ECG representation of a single heartbeat.

Preferably, the first step in ECG feature extraction is to identify each heart beat, which may be achieved by identifying the QRS complex. Several standard R-wave detection and QRS detection algorithms are known, such as that disclosed by Kohler et al., *The Principles of Software QRS Detection*, IEEE Engineering in Medicine and Biology (2002), and any of these would be suitable to detect the QRS complex. In addition, the P-wave and T-waves may also be identified such that a single heartbeat can then be defined from the beginning of the P-wave to the end of the T-wave, as shown in FIG. 6.

The precise selection of ECG features preferably depends on the resolution of the sampled and digitized ECG signal, and several components may not be adequately determined for low resolution systems. This would then result in a reduced subset of ECG features, but the same principals discussed below would still apply. Features extracted from the ECG signal may generally be divided into one of four categories: 1) morphological features, 2) transform features, 3) non-linear features, and 4) parametric modeling features.

Morphological features refer to features describing the basic geometric shape. Morphological features preferably include measurements such as the P-R interval, the S-T interval, the Q-T interval, the width of the QRS peak at 60% of the baseline level, the amplitude of the P-wave to the baseline level, the amplitude of R-wave to the baseline level, the amplitude of the T-wave to the baseline level, the amplitude of the baseline level to the Q-wave, and fitting straight lines to the Q-R and the R-S points and then calculating the angle between the resultant lines.

Transform features and nonlinear features refer to features describing details not clearly visible to the human eye (frequency components, fractal features, etc.). Transform features preferably include the average relative power in specific frequency bands that are preferably calculated using autoregressive (parametric) models. This is done, for example, by calculating the spectrum over a frequency range 1 . . . N, dividing the range into sub-bands, averaging the power in each sub-band, and then normalizing by the total power over 1-N for each sub-band. Each of these results in a new scalar feature in a feature vector. Transform features may also include wavelet coefficients, which are obtained by taking the wavelet transform of the heart beat and then selecting a subset of coefficients for use as components in the feature vector. Transform features can also include other transforms, such as cepstral transforms and discrete cosine transforms. With respect to non-linear features, these preferably include fractal dimensions of an entire heart beat, correlation dimensions of an entire heart beat, and Luypanov exponents.

Parametric modeling refers to curve fitting and then using a reduced set of coefficients from the resultant curve fit. This includes, for example, fitting a simple linear prediction or AR(MA) model to the curve of order n and then using these n points as a subcomponent of the feature vector.

Following feature extraction, the data is preferably scaled and subjected to post-processing to enhance the results of feature extraction. Preferably, post-processing preferably includes a dimension reduction method, e.g., principal components analysis, which, as described, finds a limited set important feature combinations known as principal components. Post-processing can also include calculating the class for n consecutive heart beats and then only if a predetermined percentage of these (90% etc.) all agree on the same result, is the individual assigned a class label or identifier. This advantageously allows for some tolerance of faulty QRS detection as well as artifact. Alternatively, pre-processing may include averaging n heart beats prior to feature extraction. Additional post processing may include combining the results of the ECG recognition with that of alternative biometrics before a final decision is made.

The particular learning algorithm used with the present invention can be selected from one of many algorithms known in the art, for example, linear discriminate functions, probability distribution, estimation, and clustering, support vector and other kernel machines, neural networks, and/or boosting algorithms. As discussed above, a preferred learning algorithm for identity confirmation is the one-class SVM by Scholkopf et al. because is fits a tight bound to a single class with no information about other classes. Thus, if a new feature vector falls within this bound, it belongs to this class or is associated with this person; otherwise it is rejected as being of this class or associated with this person.

Speech Parameter Recognition

As another example of parameter recognition, a preferred method for measuring breath and speech combinations as a specific biometric is described below in more detail. Some of these features are described in more detail in WO 2006/002338A2, published Jan. 5, 2006 and titled "Systems and Methods for Monitoring Cough". Preferably, a microphone or other sound recorder is first used to extract the following features and create associated traces from a provided audio sample: 1) sound envelope, 2) event marker trace, 3) pitch, 4) sound energy, 5) duration, and 6) peak fraction.

The sound envelope ("SE") is the trace of the audio signal that is preferably captured from a throat microphone ("MIC"), and downsampled from 1500 Hz to 50 Hz. Every 30 data points are preferably normalized and summed to give a low resolution envelope.

The event marker trace ("EVT") is a binary trace preferably at the same resolution as the SE trace. It is ON when the SE trace rises above a threshold (e.g., 60) and goes OFF when it drops below another threshold (e.g., 30) for 3 consecutive samples.

Pitch is evaluated using the Mel cepstrum of the raw MIC trace. A cepstrum is the result of taking the Fourier Transform (FT) of the decibel spectrum as if it were a signal. The cepstrum is preferably defined as the FT of the log (with unwrapped phase) of the FT (cepstrum of signal=FT(log(FT (the signal))+j2πm), where m is the integer required to properly unwrap the angle of the complex log function.

There is a real cepstrum and a complex cepstrum. The real cepstrum preferably uses the logarithm function defined for real values, while the complex cepstrum uses the complex logarithm function defined for complex values as well. The complex cepstrum holds information about magnitude and phase of the initial spectrum, allowing reconstruction of the signal. The real cepstrum only uses the information of the magnitude of the spectrum.

The cepstrum is an excellent feature vector for representing the human voice and musical signals. For such applications, the spectrum is preferably first transformed using the Mel frequency bands. The result is called the Mel Frequency Cepstral Coefficients (MFCC), and can be used for voice identification, pitch detection and other analysis. This is a result of the cepstrum advantageously separating the energy resulting from vocal cord vibration from the "distorted" signal formed by the rest of the vocal tract.

Sound energy is the integral of the SE trace over the duration of the EVT event. Duration is the length in milliseconds of the EVT ON period (i.e., sound event). Peak fraction refers to the peak of the SE trace for each event expressed as a fraction of the total EVT duration (e.g., (Peak location-Start)/(End-Start)).

The EVT trace is then preferably used to mark sections of the breath traces, where the following additional features are extracted:

ViVol, which is the inspired tidal volume of the breath that begins just preceding the EVT marking;

Hfb, which is the raw abdominal contribution to tidal volume band bandpass-filtered between 1 and 5 Hz;

Lfb, which is the rw abdominal contribution to tidal volume band bandpass-filtered between 0.1 and 1 Hz;

Maximum deflection, which is calculated for both Hfb and Lfb. The maximum peak—trough of consecutive peaks and troughs are determined for these filtered traces during each EVT;

Insp./Exp. ratio, which is the ratio of the percentage of the EVT during inspiration and that during expiration;

Center fraction, which is the location of the minimum trough is calculated expressed as a fraction of the event time;

Turning points, which is the number of peaks and troughs over the duration of the EVT ON;

AB baseline, which is the mean value of abdominal contribution to tidal volume band for 5 seconds before and after the event; and Phase, which is the phase difference between the ribcage contribution to tidal volume band and the abdominal contribution to tidal volume band.

Following feature extraction, the data is preferably scaled. Next, it is subject to a dimension reduction process, e.g., principal components analysis, which finds a limited number of significant combinations, i.e., that account for a large part of the data variance. Based on the identified combination of all these extracted features, a reduced-dimension feature vector representative of breath and speech is created and processed to train a classifier.

5.4 EXAMPLES

The present invention for identity confirmation is illustrated by the following example of a method of physiological parameter feature extraction for ECG and speech that is merely for the purpose of illustration and are not to be regarded as limiting the scope of the invention or the manner in which it can be practiced.

ECG Parameter Recognition

Figure 7:
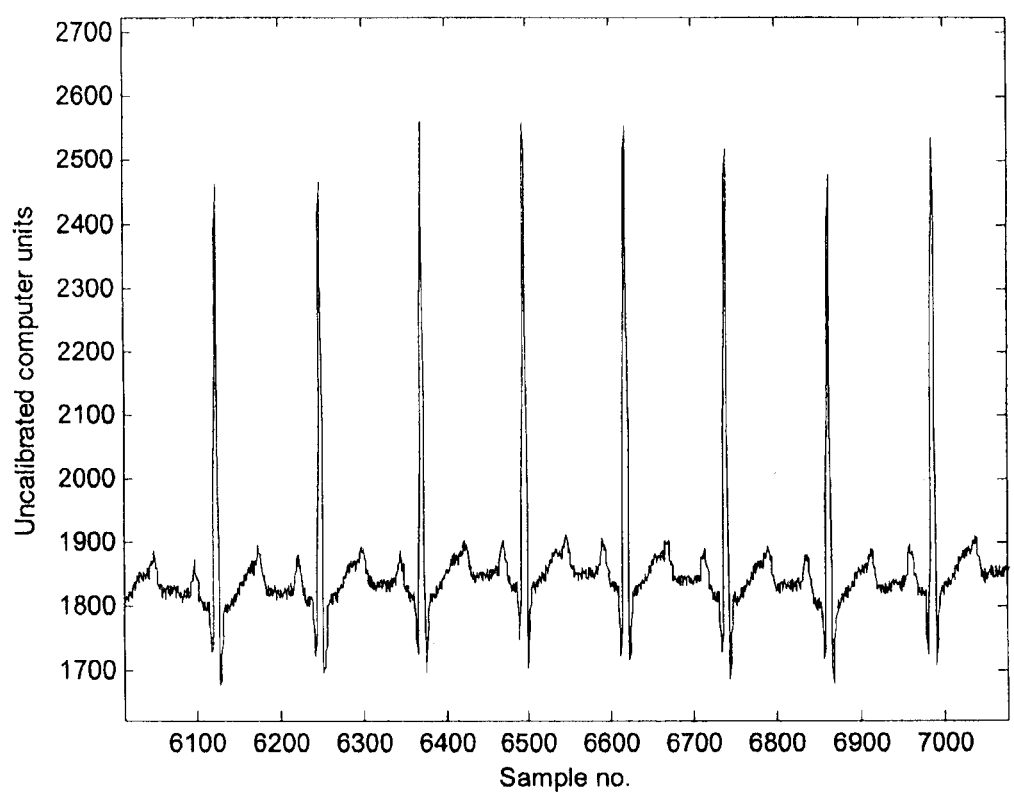
FIG. 7 depicts a segment of an ECG record.

Six subjects (i.e. classes), 4 male and 2 female, each wore the LIFESHIRT® ambulatory monitoring garment by Vivometrics, Inc. (Ventura, Calif.) with ECG sensors and stood quietly for 30 seconds of recording. Each subject was given a different class label 1 through 6, and the ECG was sampled at 200 Hz. It was preferable to sample at a higher rate as not all of the above-mentioned features were easily distinguishable at 200 Hz. FIG. 7 shows a segment of a typical ECG record for subject 2.

Figure 8:
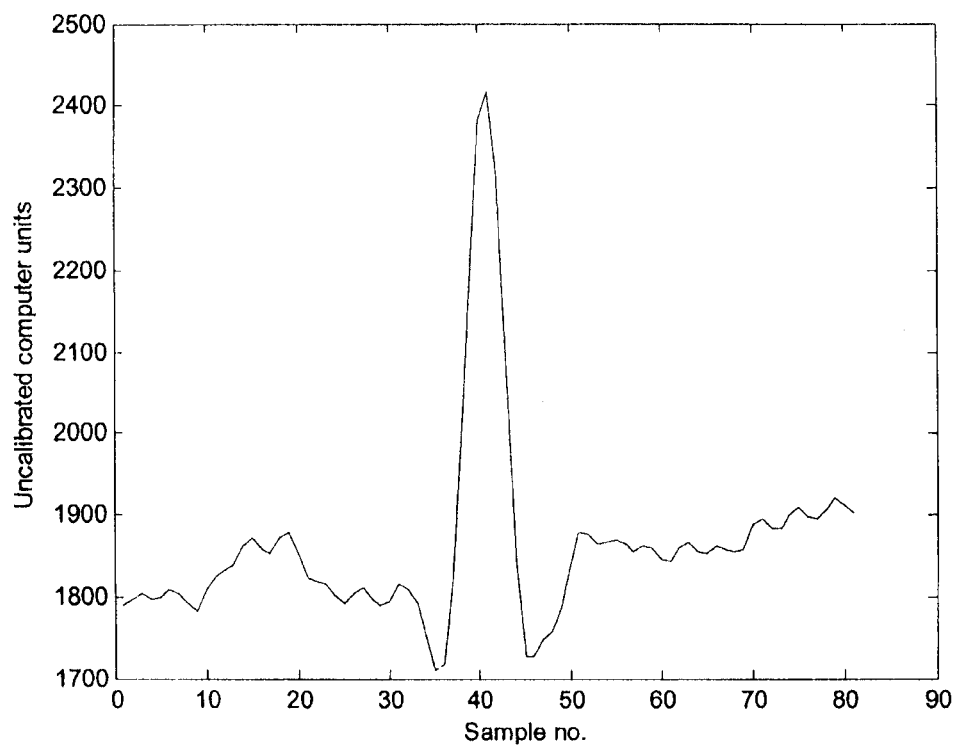
FIG. 8 depicts a QRS complex.

After sampling, QRS detection was performed on the ECG signal for each subject, which resulted in extracted QRS complexes as shown in FIG. 8, for example, for subject 2. Additionally, Table 1 shows the number of extracted QRS complexes for each subject.

TABLE 1

| Subject | No. of QRS complex's |
|---------|----------------------|
| 1 | 155 |
| 2 | 186 |
| 3 | 199 |
| 4 | 168 |
| 5 | 237 |
| 6 | 201 |

The following 11 features were extracted from each ECG QRS complex (note that all of the morphological features are normalized in some way so that they are scale independent):

1. (R-wave peak—left baseline)/left baseline;
2. (R-wave peak—right baseline)/right baseline;
3. (left baseline—min of Q or S wave)/left baseline;
4. (right baseline—min of Q or S wave)/right baseline;
5. (R wave peak—Q wave peak)/R wave peak;
6. (R wave peak—S wave peak)/R wave peak;
7. Q-R interval/length QRS;
8. location of S wave/length QRS;
9. standard deviation of QRS/mean of QRS;
10. energy in 1-4 Hz band/total energy; and
11. energy in 4-16 Hz band/total energy.

Figure 9:
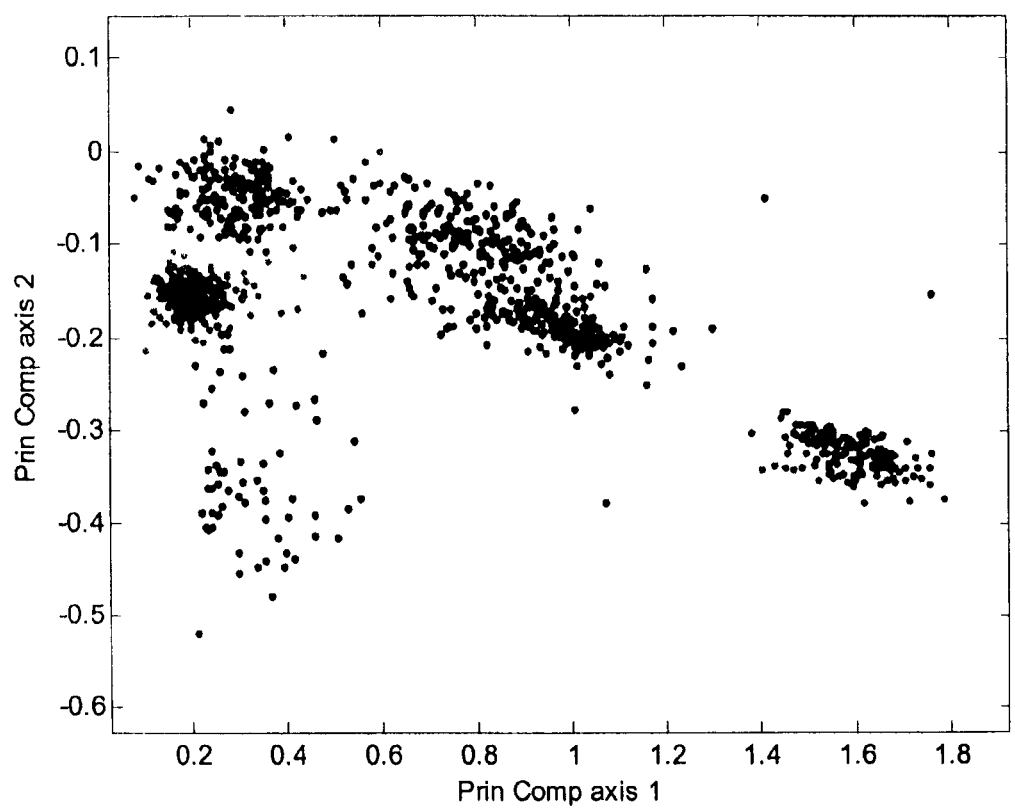
FIG. 9 depicts the plot of a principle components analysis.

Normalization or scaling was preferably achieved using two baselines, which were preferably the mean values of the first 20 and last 20 samples. Thus, the feature vector had a dimension of 14. Each of the features were then scaled to a value between 0 and 1, and then dimension reduction techniques were applied. To illustrate the idea, a principle components analysis was performed on the data to reduce the results to a dimension of 2 so that a plot for each subject could be created. An example of such a plot is illustrated in FIG. 9, which clearly shows that decision boundaries may relatively easily be drawn between data groups. These boundaries would be even more improved for analysis of more components.

In a subsequent classification step, 5 components were used, as well as an SVM. To get a measure of performance, 10 groups of cross validation tests were performed, a set of nine of these groups were used to train the classification methods, and a set of the one remaining group was used to test the classification method. Many different training and test set variations were used. The training data was never included in the test data. The accuracy for each test was the number of correct classes/total number of classes, and then the data was pooled to get a single number for the accuracy of the test.

The results showed that the total cross-validation accuracy using 2 principle components was 94.6632%, while the total cross-validation accuracy using 5 principle components was 97.9003%. This accuracy was on a heart beat by heart beat basis. Assuming that about 4 out of 5 consecutive heart beats must be the same for the individual to be classified, this will probably increase to about 100% accuracy. A potential reason for some misclassification was due to imperfect QRS detection and noise. This was minimized by having the subjects stand quietly, and will probably be increased under different testing and sampling circumstances.

This certainly proved the validity of the system for small databases. A higher sample rate will provide more accurate features when increasing the number of individuals (i.e., classes).

Speech Parameter Recognition

Four subjects (i.e. classes), 2 male and 2 female, spoke casually for 15 minutes each. Each subject wore the LIFESHIRT® with abdominal and ribcage sensor bands, and were in both seated and standing postures. Each subject was given a different class label 1 through 4. The respiratory IP sensors were sampled at 50 Hz, and a throat microphone that sampled at 1500 Hz was used.

A simple feature vector of dimension 8 was formed, which included pitch, Lfb deflection, Hfb deflection, ViVol, Insp./Exp. ratio, duration, turning points, and center fraction. Each feature was scaled or normalized between 0 and 1, and then dimension reduction techniques were applied by performing a principle components analysis to reduce the date to a dimension of 2. The results indicated that such parameter recognition techniques, which include extraction of the above-listed speech-related features, followed by scaling and dimension reduction of the data, can be applied to differentiate sufficiently between speech or audio events for various classes or persons so that they can be automatically classified.

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the scope of the present invention.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for verifying a person's identity, comprising:
    measuring a biometric of a person whose identity is known, wherein the biometric comprises a respiratory biometric, and setting a baseline for the biometric based on the measurement, wherein the thoracic or abdominal girth of the person is measured;
    calculating an acceptable variation range for the biometric, wherein the acceptable variation range has upper and lower bounds that differ by a percentage of the measured biometric, and is based on the baseline and the normal deviation for the biometric across a population sample of people;
    storing the acceptable variation range in a memory;
    obtaining a password or key from a person to be verified;
    comparing the obtained password or key to a plurality of known passwords or keys to determine a likely identity of the person to be verified, wherein each of the plurality of known passwords or keys are associated with a specific person;
    obtaining a measurement of the biometric from the person to be verified and setting a value for the biometric for the person to be verified; and
    comparing the value of the biometric for the person to be verified to a stored acceptable variation range of a specific person associated with the obtained password or key to verify the likely identity of the person to be verified.

2. The method of claim 1, wherein the respiratory biometric comprises a respiratory rate, a minute ventilation, a tidal volume, an inspiratory flow rate, an expiratory flow rate, a presence of cough, or a presence of apnea or hypoapnea.

3. The method of claim 1, wherein the girth is measured by inductive plethysmography.

4. The method of claim 1, wherein measuring the respiratory biometric comprises:
    instructing the person whose identity is known and the person to be verified to perform one or more maneuvers; and
    measuring at least one respiratory pattern exhibited by the person whose identity is known and the person to be verified during performance of the maneuvers, wherein the baseline respiratory biometric for the person whose identity is known and the set value for the respiratory biometric for the person to be verified comprise at least one measured respiratory pattern.

5. The method of claim 4, wherein the at least one respiratory pattern is measured over a period time during the performance of the maneuvers.

6. The method of claim 4, wherein at least one maneuver comprises performing a predetermined sequence of breaths.

7. The method of claim 4, wherein at least one maneuver comprises performing a predetermined sequence of physical movements.

8. The method of claim 1, wherein the biometric comprises a plurality of physiological parameters.

9. A method for verifying a person's identity, comprising:
    measuring a biometric of a person whose identity is known, wherein the biometric comprises a respiratory biometric, and setting a baseline for the biometric based on the measurement, wherein the thoracic or abdominal girth of the person is measured;
    calculating an acceptable variation range for the biometric, wherein the acceptable variation range has upper and lower bounds that differ by a percentage of the measured biometric, and is based on the baseline and the normal deviation for the biometric across a population sample of people;

storing the acceptable variation range in a memory;

obtaining a measurement of the biometric from a person to be verified using an ambulatory measuring device and setting a value for the biometric for the person to be verified; and comparing the value of the biometric for the person to be verified to a database including a plurality of person-specific acceptable variation ranges for a population to verify the identity of the person to be verified.

10. The method of claim 9, wherein the ambulatory measuring device comprises a garment that is worn by the person to be verified.

11. The method of claim 9 further comprising, prior to obtaining the measurement of the biometric from the person to be verified:
    obtaining from the person to be verified a password, key, or electrocardiogram; and
    comparing the obtained password, key, or electrocardiogram to a known database of passwords, keys, or electrocardiograms to determine a likely identity of the person to be verified;
    wherein the value of the biometric for the person to be verified is compared to an acceptable variation range of a person associated with the password, key, or electrocardiogram to verify the likely identity of the person to be verified.

12. The method of claim 8, wherein the plurality of physiological parameters includes at least one of the following: a cardiac parameter, a posture/activity parameter, a temperature parameter, an EEG parameter, an EOG parameter, EMG parameter, a vocal parameter, and a gait parameter.

13. The method of claim 1, wherein the person whose identity is known and the person to be verified are the same person.

14. The method of claim 9, wherein the person whose identity is known and the person to be verified are the same person.

15. A method for verifying a person's identity, comprising:
    measuring a biometric of a person whose identity is known, wherein the biometric comprises an ECG parameter, and setting a baseline for the biometric based on the measurement;
    calculating an acceptable variation range for the biometric, wherein the acceptable variation range has upper and lower bounds that differ by a percentage of the measured biometric,
    and is based on the baseline and the normal deviation for the biometric across a population sample of people;
    storing the acceptable variation range in a memory;
    obtaining a password or key from a person to be verified;
    comparing the obtained password or key to a plurality of known passwords or keys to determine a likely identity of the person to be verified, wherein each of the plurality of known passwords or keys are associated with a specific person;
    obtaining a measurement of the biometric from the person to be verified and setting a value for the biometric for the person to be verified; and
    comparing the value of the biometric for the person to be verified to a stored acceptable variation range of a specific person associated with the obtained password or key to verify the likely identity of the person to be verified.

16. A method for verifying a person's identity, comprising:
    measuring a biometric of a person whose identity is known and setting a baseline for the biometric based on the measurement;
    calculating an acceptable variation range for the biometric, wherein the acceptable variation range has upper and lower bounds that differ by a percentage of the measured biometric,
    and is based on the baseline and the normal deviation for the biometric across a population sample of people;
    storing the acceptable variation range in a memory;
    obtaining a password or key from a person to be verified;
    comparing the obtained password or key to a plurality of known passwords or keys to determine a likely identity of the person to be verified, wherein each of the plurality of known passwords or keys are associated with a specific person;
    obtaining a measurement of the biometric from the person to be verified and setting a value for the biometric for the person to be verified;
    comparing the value of the biometric for the person to be verified to a stored acceptable variation range of a specific person associated with the obtained password or key to verify the likely identity of the person to be verified;
    obtaining a fingerprint, a retinal scan, an electrocardiogram, or a DNA scan from the person to be verified;
    comparing the obtained fingerprint, retinal scan, electrocardiogram, or DNA scan to a plurality of known fingerprints, retinal scans, electrocardiograms, or DNA scans to determine a likely identity of the person to be verified; and
    comparing the value of the biometric for the person to be verified to the acceptable variation range of a person associated with the obtained fingerprint, retinal scan, electrocardiogram, or DNA scan to verify the likely identity of the person to be verified.

17. A method for verifying a person's identity, comprising:
    measuring a biometric of a person whose identity is known, wherein the biometric comprises an ECG parameter, and setting a baseline for the biometric based on the measurement;
    calculating an acceptable variation range for the biometric, wherein the acceptable variation range has upper and lower bounds that differ by a percentage of the measured biometric,
    and is based on the baseline and the normal deviation for the biometric across a population sample of people;
    storing the acceptable variation range in a memory;
    obtaining a measurement of the biometric from a person to be verified using an ambulatory measuring device and setting a value for the biometric for the person to be verified; and
    comparing the value of the biometric for the person to be verified to a database including a plurality of person-specific acceptable variation ranges for a population to verify the identity of the person to be verified.

* * * * *